(12) United States Patent
Holecek et al.

(10) Patent No.: US 8,511,244 B2
(45) Date of Patent: Aug. 20, 2013

(54) METHODS AND APPARATUSES FOR ASSEMBLY OF A PERICARDIAL PROSTHETIC HEART VALVE

(71) Applicant: Medtronic, Inc., Minneapolis, MN (US)

(72) Inventors: Arin N. Holecek, Minneapolis, MN (US); Carolyn Majkrzak, Minneapolis, MN (US); Janice L. Shay, Minneapolis, MN (US); Carol E. Eberhardt, Minneapolis, MN (US); David L. Kulcinski, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/656,247

(22) Filed: Oct. 19, 2012

(65) Prior Publication Data
US 2013/0055941 A1    Mar. 7, 2013

Related U.S. Application Data

(62) Division of application No. 12/424,742, filed on Apr. 16, 2009, now Pat. No. 8,312,825.

(60) Provisional application No. 61/125,202, filed on Apr. 23, 2008.

(51) Int. Cl.
*D05B 39/00* (2006.01)
*A61F 2/24* (2006.01)

(52) U.S. Cl.
USPC ............... 112/475.08; 112/470.14; 623/2.13

(58) Field of Classification Search
USPC ............ 112/475.01–475.08, 470.01–470.18; 623/2.1–2.19, 2.3, 2.41, 2.42
See application file for complete search history.

(56) References Cited

U.S. PATENT DOCUMENTS

| 517,860 A | * | 4/1894 | Hooper ................. 38/102.2 |
| 3,657,744 A | | 4/1972 | Ersek |
| 3,671,979 A | | 6/1972 | Moulopoulos |

(Continued)

FOREIGN PATENT DOCUMENTS

| CN | 2007-100074433 | 8/2007 |
| DE | 195 32 846 | 3/1997 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Ismael Izaguirre

(57) ABSTRACT

A method of assembling a prosthetic valve using sheets of material, such as pericardium material, polymer or bioengineered film, or other material. The method provides an accurate and repeatable system of making pericardial valves in which sheets or pieces of material are held securely in place relative to each other throughout the steps of assembling the valve. In addition, methods of the present invention include maintaining consistent alignment of the fixtures and pericardium material throughout the valve assembly process and utilize features that make the tooling components easy to assemble and handle. Certain aspects of the invention can be used to help establish a repeatable sewing and cutting technique for creating a pattern shape for valve leaflets, establishing stitch lengths, and determining the exact placement of stitches.

13 Claims, 10 Drawing Sheets

(56) References Cited

U.S. PATENT DOCUMENTS

| | | |
|---|---|---|
| 3,714,671 A | 2/1973 | Edwards et al. |
| 3,755,823 A | 9/1973 | Hancock |
| 3,868,956 A | 3/1975 | Alfidi et al. |
| 3,988,993 A | 11/1976 | Brophy |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,229,890 A * | 10/1980 | Dropinski .................... 38/102.1 |
| 4,265,694 A | 5/1981 | Boretos |
| 4,297,749 A | 11/1981 | Davis et al. |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,587,910 A | 5/1986 | Raines |
| 4,592,340 A | 6/1986 | Boyles |
| 4,610,688 A | 9/1986 | Silvestrini et al. |
| 4,639,964 A | 2/1987 | Binder |
| 4,647,283 A | 3/1987 | Carpentier et al. |
| 4,648,881 A | 3/1987 | Carpentier et al. |
| 4,665,906 A | 5/1987 | Jervis |
| 4,681,908 A | 7/1987 | Broderick et al. |
| 4,682,551 A | 7/1987 | Toman |
| 4,694,766 A | 9/1987 | Wickers et al. |
| 4,710,192 A | 12/1987 | Liotta et al. |
| 4,725,274 A * | 2/1988 | Lane et al. .................... 623/2.18 |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,994,077 A | 2/1991 | Dobben |
| 5,002,559 A | 3/1991 | Tower |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,085,635 A | 2/1992 | Cragg |
| 5,089,015 A | 2/1992 | Ross |
| 5,141,140 A * | 8/1992 | Moffett-Hall .................... 223/52 |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,355,792 A * | 10/1994 | MacNaughton et al. .. 101/127.1 |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,488,789 A * | 2/1996 | Religa et al. .................... 38/102.2 |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,560,309 A | 10/1996 | Conley et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,667,523 A | 9/1997 | Bynon et al. |
| 5,674,277 A | 10/1997 | Freitag |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,891,191 A | 4/1999 | Stinson |
| 5,902,937 A | 5/1999 | Amrani et al. |
| 5,906,619 A | 5/1999 | Olson et al. |
| 5,913,842 A | 6/1999 | Boyd et al. |
| 5,915,318 A | 6/1999 | Iwasaki et al. |
| 5,925,063 A | 7/1999 | Khosravi |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,245 A | 12/2000 | Jayaraman |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,245,102 B1 | 6/2001 | Jayaraman |
| 6,248,116 B1 | 6/2001 | Chevillon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |

| Patent Number | Date | Inventor |
|---|---|---|
| 6,352,708 B1 | 3/2002 | Duran et al. |
| 6,371,970 B1 | 4/2002 | Khosravi et al. |
| 6,371,983 B1 | 4/2002 | Lane |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,556,646 B2 | 7/2009 | Yang et al. |
| 7,739,971 B2 | 6/2010 | Chambers et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |

| | | |
|---|---|---|
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Seguin et al. |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua et al. |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Jantz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |

| | | |
|---|---|---|
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004688 A1 | 1/2008 | Spenser et al. |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0240264 A1 | 9/2009 | Tuval et al. |
| 2009/0240320 A1 | 9/2009 | Tuval |
| 2009/0287299 A1 | 11/2009 | Tabor et al. |
| 2010/0011564 A1 | 1/2010 | Millwee et al. |
| 2010/0018447 A1 | 1/2010 | Holecek et al. |
| 2010/0023120 A1 | 1/2010 | Holecek et al. |
| 2010/0036484 A1 | 2/2010 | Hariton et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |

FOREIGN PATENT DOCUMENTS

| | | |
|---|---|---|
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 48 814 | 9/2000 |
| DE | 100 49 812 | 4/2002 |
| DE | 100 49 813 | 4/2002 |
| DE | 100 49 815 | 4/2002 |
| EP | 0103546 | 3/1984 |
| EP | 0597967 | 12/1994 |
| EP | 0850607 | 7/1998 |
| EP | 1057459 A1 | 6/2000 |
| EP | 1057460 A1 | 6/2000 |
| EP | 1088529 | 4/2001 |
| EP | 1255510 | 11/2002 |
| EP | 0937439 B1 | 9/2003 |
| EP | 1340473 | 9/2003 |
| EP | 0819013 | 6/2004 |
| FR | 2788217 | 12/1999 |
| GB | 2056023 | 3/1981 |
| GB | 2433700 | 12/2007 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |
| WO | 2005/027790 | 3/2005 |
| WO | 2005/046528 | 5/2005 |
| WO | 2008/047354 | 4/2008 |
| WO | 2008/079962 | 7/2008 |
| WO | 2008/100599 | 8/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Henzel, et al., "Complications of percutaneous aortic valve replacement: experience with the Criber-Edwards™ percutaneous heart valve," EuroIntervention Supplements (2006), 1 (Supplement A) A3-A8.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pasupati et al., "Transcatheter Aortic Valve Implantation Complicated by Acute Structural Valve Failure Requiring Immediate Valve in Valve Implantation," Heart, Lung and Circulation 2010; doi:10.1016/j.hlc.2010.05.006.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Webb, et al., "Percutaneous Aortic Valve Implantation Retrograde from the Femoral Artery," Circulation (2006), 113;842-850.

Expert report of Dr. Nigel Buller, dated Jan. 12, 2009, Edwards' United Kingdom action for invalidity, Claim No. HC 08CO0934 (83 pages).

Expert report of Dr. Nigel Buller, non-confidential annex—infringement, dated Jan. 12, 2009, Edwards' United Kingdom action for invalidity, Claim No. HC 08CO0934 (12 pages).

Expert report of Dr. Rodolfo Quijano, dated Jan. 9, 2009, *Edwards' LifeSciences v. Cook Biotech Incorporated*, United Kingdom action for invalidity, Claim No. HC 08CO0934 (18 pages).

First Expert report of Prof. David Williams, dated Jan. 12, 2009, Edwards' United Kingdom action for invalidity, Claim No. HC 08CO0934 (41 pages).

Pavcnik et al., "Aortic and venous valve for percutaneous insertion," Min. Invas. Ther. & Allied Techol. 2000, vol. 9, pp. 287-292.

First Expert report of Dr. Nigel Person Buller (30 pages), *Corevalve, Inc. v. Edwards Lifesciences AG and Edwards Lifesciences PVT, Inc.*, High Court of Justice—Chancery Division Patents Court, United Kingdom, Case No. HC-07-C01243, Apr. 2008.

* cited by examiner

METHODS AND APPARATUSES FOR ASSEMBLY OF A PERICARDIAL PROSTHETIC HEART VALVE

CROSS-REFERENCE TO RELATED APPLICATION

The present application is a division of and claims priority to U.S. patent application Ser. No. 12/424,742 filed Apr. 16, 2009, now allowed; which claims priority to U.S. Provisional Application No. 61/125,202, filed Apr. 23, 2008, and titled "Methods and Apparatuses for Assembly of a Pericardial Prosthetic Heart Valve" the entire contents of which are incorporated herein by reference in its entirety.

TECHNICAL FIELD

The present invention relates generally to treatment of cardiac heart disease. More particularly, the present invention relates to implantable valve prostheses for implantation into the cardiac system.

BACKGROUND

All four of the valves in the heart are passive structures in that they do not themselves expend any energy and do not perform any active contractile function. They consist of moveable "leaflets" that open and close in response to differential pressures on either side of the valve. The problems that can develop with valves can generally be classified into two categories: (1) stenosis, in which a valve does not open properly, and (2) insufficiency (also called regurgitation), in which a valve does not close properly. Stenosis and insufficiency may occur concomitantly in the same valve or in different valves. Both of these abnormalities increase the workload placed on the heart. The severity of this increased stress on the heart and the patient, and the heart's ability to adapt to it, determine the treatment options that can be pursued. In some cases, medication can be sufficient to treat the patient, which is the preferred method of treatment; however, in many cases defective valves have to be repaired or completely replaced in order for the patient to live a normal life.

The two general categories of valves that are available for implantation into the cardiac system are mechanical valves and bioprosthetic or tissue valves. Mechanical valves have been used for many years and encompass a wide variety of designs that accommodate the blood flow requirements of the particular location where they will be implanted. Although the materials and design features of these valves are continuously being improved, they do increase the risk of clotting in the blood stream, which can lead to a heart attack or stroke. Thus, mechanical valve recipients must take anti-coagulant drugs for life to lessen the potential for blood clot formation. Further, mechanical valves can sometimes suffer from structural problems that may force the patient to have additional surgeries for further valve replacement.

Bioprosthetic valves, which are also referred to as prosthetic valves, generally include both human tissue valves and animal tissue valves. The designs of these bioprosthetic valves are typically relatively similar to the design of the natural valves of the patient and advantageously do not require the use of long-term anti-coagulant drugs. Human tissue valves are typically not available in large quantities, however, since they must be removed from deceased persons who have elected organ donation. On the other hand, animal tissue valves are more widely available for the patients who require valve replacement due to the large numbers of animals routinely processed at meat processing facilities, for example. The most common types of animal tissue valves used include porcine aortic valves, and bovine and porcine pericardial valves, some of which are incorporated with a stent before being implanted in a patient. In the case of pericardial valves, the use of pericardial material to design and make the heart valves provides a much larger range of options than is available when using only harvested valves.

In order to manufacture these pericardial valves, a number of steps must be performed on one or more pieces of pericardium material, where this work is typically done by highly-skilled operators in a controlled environment. Even under these conditions, however, there is concern that minor variations in the valves can occur due to slight differences in the techniques used by individual operators and the variability of materials used. In order to minimize these variations, there is a need to provide reproducible and simple tooling and methods for manufacturing pericardial valves.

SUMMARY

The present invention is directed to prosthetic cardiac valves and methods of making such valves. In one embodiment, the invention involves methods and tooling for making valves using sheets or pieces of material, such as pericardium material, polymer or bioengineered film, or other material. The tooling and processes provide an accurate and repeatable system of making pericardial valves in which sheets or pieces of pericardium material are held securely in place relative to each other throughout all of the steps or making the valve. In addition, the methods of the present invention include maintaining consistent alignment of the fixtures and pericardium material throughout the valve assemble process and utilize features that make the tooling components easy to assemble and handle. Certain aspects of the invention can be used to help establish a repeatable sewing and cutting technique for creating a pattern shape for valve leaflets, establishing stitch lengths, and determining the exact placement of stitches.

In one aspect of the invention, a method is provided to secure two pieces of tissue material to each other in a predetermined series of vertical segments connected by arches or arcuate portions that will make up multiple leaflets of a valve. Once the tissue layers are secured to each other in a desired configuration, the tissue assembly can be formed into a tube so that the arches and vertical segments make the leaflets of a valve. The valve can then be secured to a stent to make a stented valve, if desired. In such a configuration, the stent structure may be compressible and expandable to facilitate percutaneous insertion into the heart of a patient, such as with a self-expanding stent or with a stent that is expandable when subjected to outward radial force.

In another aspect of the invention, individual leaflets are constructed, which can then be made into a multi-leaflet valve that will have more than one side seam when assembled into a tubular valve. The leaflets are each constructed from a wall layer of tissue and a leaflet layer of tissue and again are assembled in a way that involves repeatable sewing techniques for creating consistently shaped valve leaflets.

BRIEF DESCRIPTION OF THE DRAWINGS

The present invention will be further explained with reference to the appended Figures, wherein like structure is referred to by like numerals throughout the several views, and wherein: The present invention will be further explained with reference to the appended Figures, wherein like structure is referred to by like numerals throughout the several views, and wherein.

DETAILED DESCRIPTION

Heart valves made using the methods and processes of the invention can be used for replacement of pulmonary valves, aortic valves, mitral valves, or tricuspid valves, in accordance with the methods and valve constructions of the invention described herein. Alternatively, the valves of the invention can be used to replace a failed bioprosthesis, such as in the area of an aortic valve or mitral valve, for example. The shape, size, material, and configuration of the outer tubular portion of the heart valves described herein can specifically be designed and chosen for the type of valve that is being produced. The valves of the invention can include stented or stentless valves, but in either case, the valves are preferably compressible to a reduced diameter during the implantation process, such as transcatheter implantation, and can be capable of being expanded to a large diameter once they are is their desired implantation location. The valve assemblies can be used as a surgical sutureless or apical implant, and can be utilized in percutaneous replacement of cardiac valves, for example. One exemplary method for assembling a stented valve of the invention generally includes the manufacture and preparation of a valve segment, then a subsequent mounting or attachment of the prepared valve segment to a stent.

Figure 1:
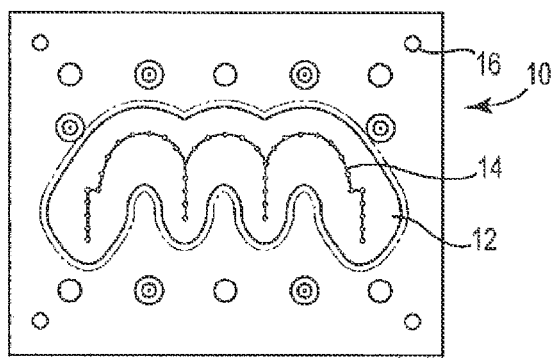
FIG. 1 is a top view of a top plate of a sewing fixture frame, in accordance with one aspect of the invention.

Referring now to the Figures, wherein the components are labeled with like numerals throughout the several Figures, and initially to FIGS. 1-9, a number of tooling components are illustrated that are used in accordance with the processes and methods of the invention for assembly of a pericardial valve. In particular, FIG. 1 is a top view of a top plate 10 of a sewing fixture frame, in accordance with one aspect of the invention. Top plate 10 includes a central opening 12 though which an exemplary stitching pattern 14 is visible, such as can be provided by a sewing fixture template, as described below. The central opening 12 can be configured differently than shown, but should be small enough that the surrounding portions of the plate 10 provide enough material to securely hold tissue below it (i.e., to maximize the surface area of the plate that will be available to contact tissue), but should also be large enough to allow an operator to easily access the layers below it for sewing of tissue layers. The top plate 10 also includes at least one locating hole 16, each of which is positioned and sized for engagement with a locating pin of a bottom plate of a sewing fixture frame. This embodiment provides one locating hole 16 near each of the four corners of the top plate 10, although more or less locating holes 16 may be used. Top plate 10 also includes a number of additional holes located in various locations across its solid portion that can be used as tack holes for positioning the pericardial or tissue layers along with other tooling components, or for other purposes.

Figure 2:
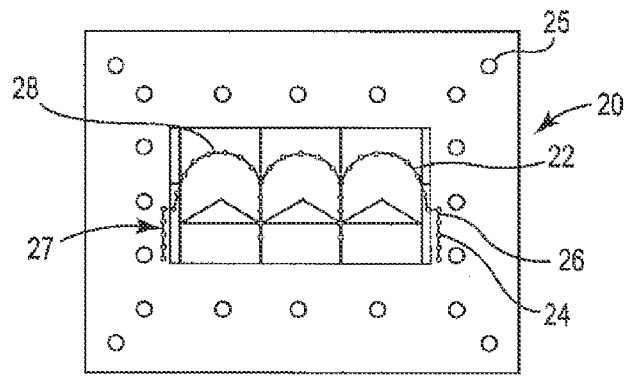
FIG. 2 is a top view of a sewing fixture template.

FIG. 2 is a top view of a sewing fixture template 20, which can be relatively thin as compared to the top plate 10. Template 20 includes a pattern 22 for sewing leaflets, which is located in generally the central area of the template. As shown, the pattern 22 can include a series of holes 24 that are spaced from each other, with adjacent holes 24 being connected by slots 26. Each hole 24 provides a location in which a needle can be pushed through the template 20 and the slots 26 provide a place for the thread or suture material to lie that extends between adjacent holes 24. The template 20 preferably also includes locating holes 25 that will align with the locating pins of a bottom plate of a sewing fixture frame in the processes of the invention. Template 20 also includes a number of additional holes located in various locations on its planar surface that can be used as tack holes for positioning the pericardial or tissue layers along with other tooling components, or for other purposes. At least some of these holes can correspond with holes of other plates or components of the invention, if desired.

The shaped portion of the pattern 22 includes vertical components 27 that correspond to leaflet commissures. The vertical components 27 are provided in pairs, where each vertical component 27 of a pair is spaced from the other vertical component 27 of the pair by a distance that represents the desired width of a leaflet. An arcuate portion 28 is also provided for each pair of vertical components 27, which extends between each pair of vertical components 27. The vertical components 27 are generally linear and are preferably also generally parallel to each other. Alternatively, the vertical components 27 can be arranged in a non-parallel configuration to provide another shape to the attachment pattern, such as a funnel shape, for example. The length of the vertical components 27 can be chosen to correspond to the desired depth of a leaflet, such that a pattern including relatively long vertical components 27 will provide bigger or deeper leaflets that a pattern having relatively short vertical components 27. Thus, the length of the vertical components 27 can advantageously be designed and/or selected to correspond with a desired depth of the leaflets, which selection is not available when using a native valve, for example. In any case, all of the vertical components 27 of a particular pattern 22 can have the same or nearly the same length in order to create leaflets that are identically or nearly identically shaped and sized for a certain valve. In that respect, all of the vertical components 27 can also be spaced at the same distance from each other, and also can be spaced at a distance form a corresponding edge that will facilitate making the width of all of the shaped portions the same for a particular piece of pericardium material. However, it is also contemplated that the vertical components 27 within a single valve configuration can have different lengths and/or can be spaced at different distances from each other in order to create a valve having leaflets that are not all identically sized and/or shaped.

Figure 3:
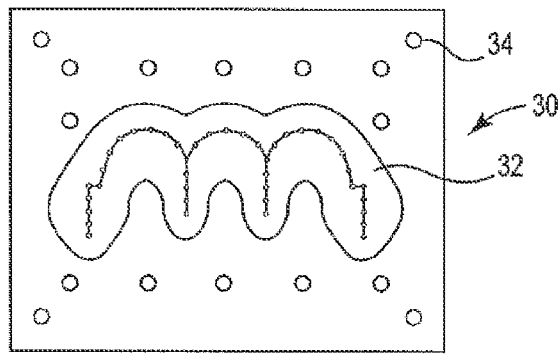
FIG. 3 is a top view of a bottom plate of a sewing fixture frame.

FIG. 3 is a top view of a bottom plate 30 of a sewing fixture frame. Bottom plate 30 includes a central opening 32 through which an exemplary stitching pattern (e.g., pattern 22) is visible. The opening 32 can generally match the opening 12 of the top plate 10, or the central opening 32 of this bottom plate 30 can be different from the central opening 12 of the top plate 10. As described above relative to the opening 12 of top plate 10, the central opening 32 of bottom plate 30 can be configured differently than shown, but should be small enough that the surrounding portions of the plate 30 can securely hold tissue adjacent to it. The opening 32 also should be large enough to allow the operator to easily access the material and/or template layers that are adjacent to it. The bottom plate 30 also includes at least one locating pin 34 extending from one of its surfaces, where this embodiment provides one locating pin 34 near each of the four corners of the bottom plate 30, although more or less locating pins 34 may be used. Bottom plate 30 also includes a number of holes located in various locations across its solid portion that can be used as tack holes for positioning the pericardial or tissue layers along with other tooling components, or for other purposes.

Figure 4:
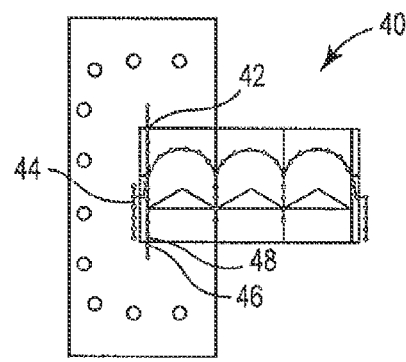
FIG. 4 is a top view of a final seam sewing fixture template.

FIG. 4 is a top view of final seam sewing fixture template 40, which includes a stitch pattern line 42 and a reference tab window 44. An exemplary sewing pattern is superimposed on top of this template 40 for illustrative purposes. As shown, the stitch pattern line 42 can include a series of holes 46 that are spaced from each other, with adjacent holes 46 being connected by slots 48. Each hole 46 provides a location in which a needle can be pushed through the materials, and the slots 48 provide a place for the thread or suture material to lie that extends between adjacent holes 46. Template 40 also includes a number of holes located in various locations across its solid portion that can be used as tack holes for positioning the pericardial or tissue layers along with other tooling components, or for other purposes. As will be described below, it is preferable that a first sewing fixture template 40 is positioned above the layers of pericardial tissue, and that a second sewing fixture template 40 is positioned below the layers of pericardial tissue during the sewing process.

Figure 5:
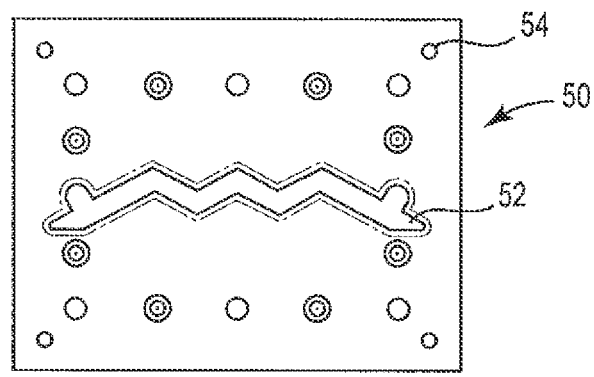
FIG. 5 is a top view of a cutting fixture top plate.

FIG. 5 is a top view of a cutting fixture top plate 50, which includes a central opening 52 that can be used as a guide during the step of cutting layers of pericardial material that are sewn together in a stitching pattern, such as the pattern 22 described above. The central opening 52 can be configured differently than shown, but should be small enough that the surrounding portions of the plate 50 can securely hold tissue below it, but should also be large enough to allow the operator to easily access the layers below it. The top plate 50 also includes at least one locating hole 54, each of which is positioned and sized for engagement with a locating pin of a bottom plate of a sewing fixture frame. This embodiment provides one locating hole 54 near each of the four corners of the top plate 50, although more or less locating holes 54 may be used. Top plate 50 also includes a number of additional holes located in various locations across its solid portion that can be used as tack holes for positioning the pericardial or tissue layers along with other tooling components, or for other purposes.

Figure 6:
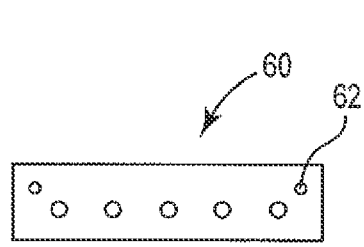
FIG. 6 is a top view of an upper cutting fixture middle plate.
Figure 7:
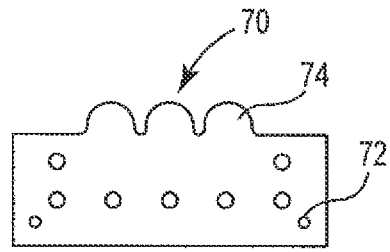
FIG. 7 is a top view of a lower cutting fixture middle plate.
Figure 11:
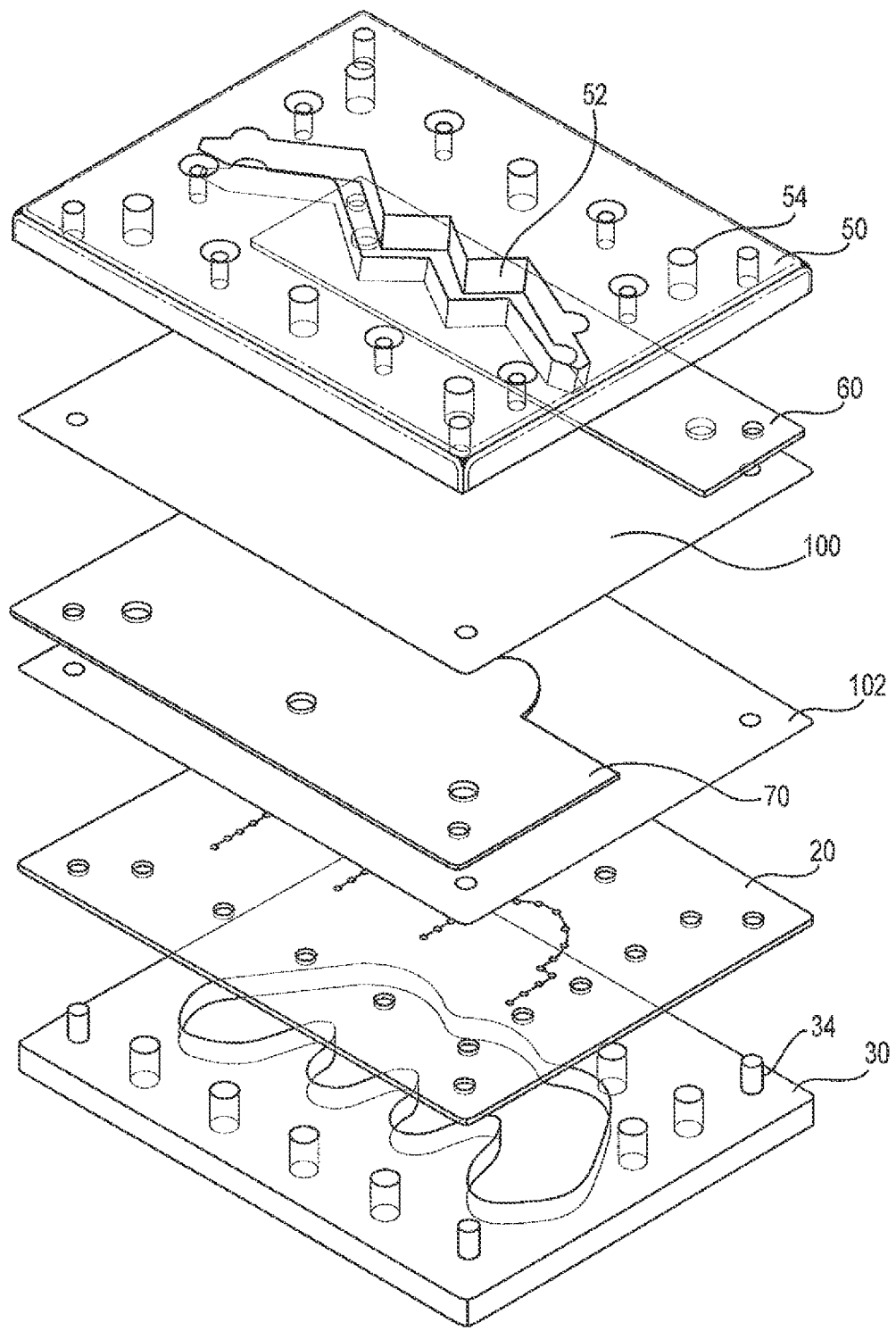
FIG. 11 is an exploded perspective view of multiple components and material layers involved in a cutting step for assembling a pericardial valve.

FIG. 6 is a top view of an upper cutting fixture middle plate 60, which is used in the cutting assembly and process as a spacer to keep a consistent relative thickness for the overall tooling stack. In particular, because a lower cutting fixture middle plate 70 of FIG. 7 will only extend across a portion of the width of the assembly (see FIG. 11), the plate 60 is positioned in the area across which the plate 70 does not extend in order to keep the thickness of the multiple tooling layers consistent within the assembly. Both plates 60, 70 have at least one locating hole 62, 72, respectively, that will each preferably be aligned with a locating pin during the cutting process, and can also include a number of additional holes located in various locations that can be used as tack holes for positioning the pericardial or tissue layers along with other tooling components, or for other purposes. As shown, plate 70 is also provided with scalloped portions 74 that are provided to generally match the shape of the pattern that has been sewn in the pericardial tissue. The material that makes up the plate 70 is preferably: (1) thin enough to cause only minimal displacement of the tissue layers relative to each other; (2) strong enough to withstand the action of a cutting mechanism; and (3) soft enough to not dull or otherwise adversely affect a cutting mechanism that contacts it.

Figure 8:
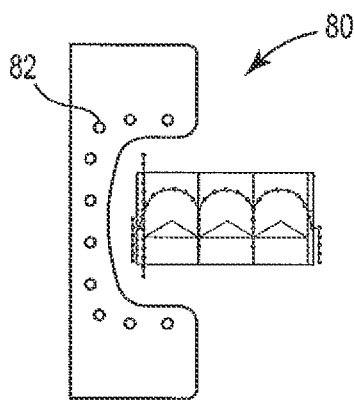
FIG. 8 is a top view of a bottom plate of a final seam sewing fixture.
Figure 9:
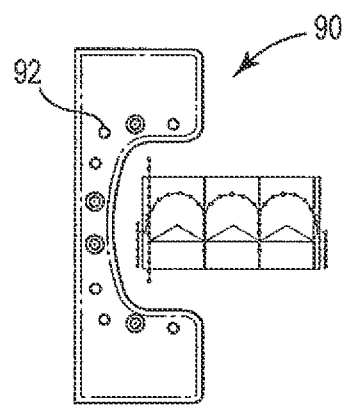
FIG. 9 is a top view of a top plate of a final seam sewing fixture.
Figure 12:
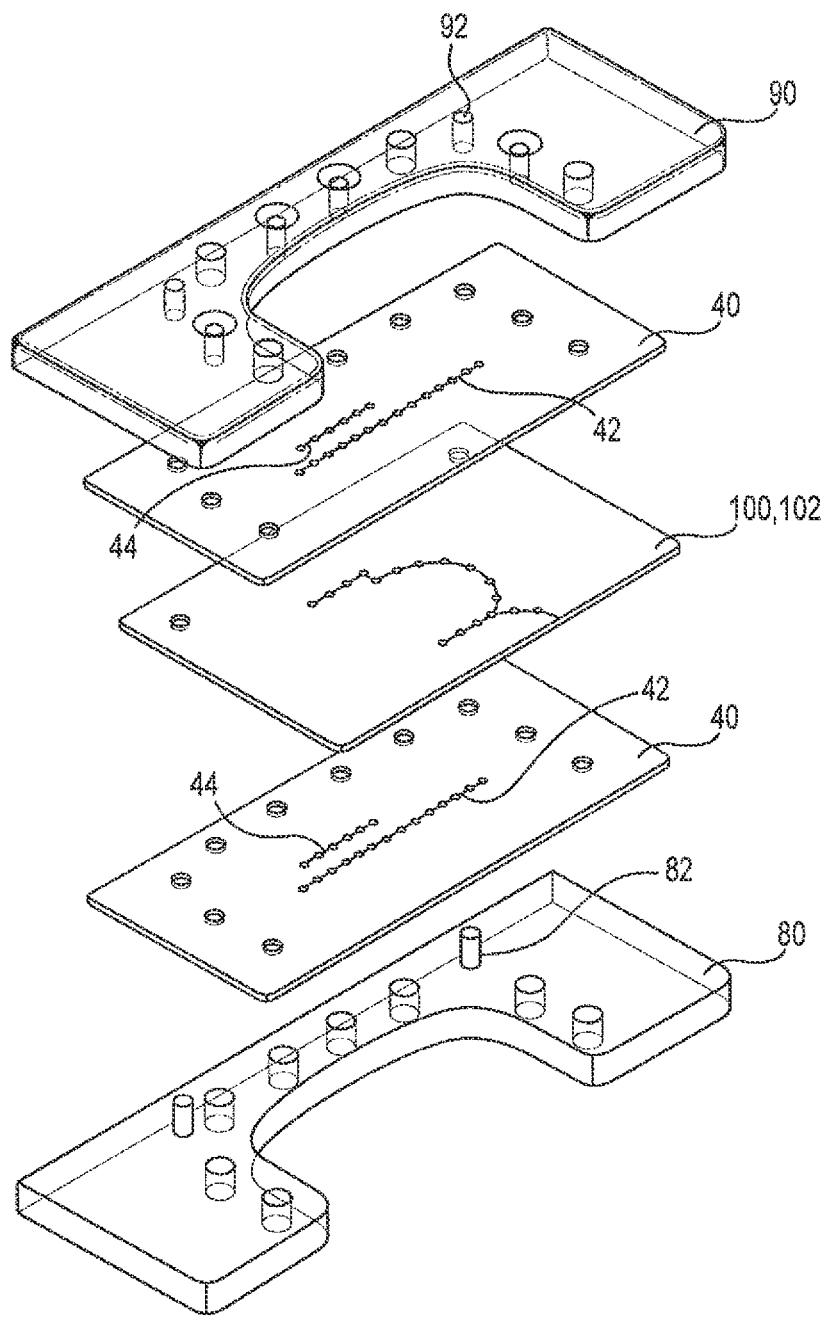
FIG. 12 is an exploded perspective view of multiple exponents and material layers involved in a final seam sewing step for assembly a pericardial valve.
Figure 13:
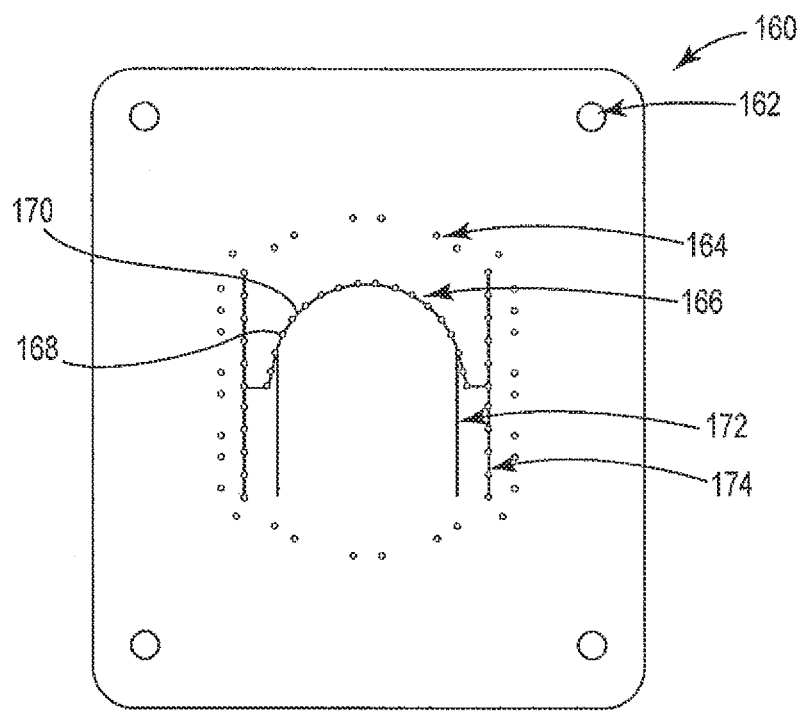
FIG. 13 is a top view of a sewing plate used for individual leaflet construction in accordance with another aspect of the invention.
Figure 14:
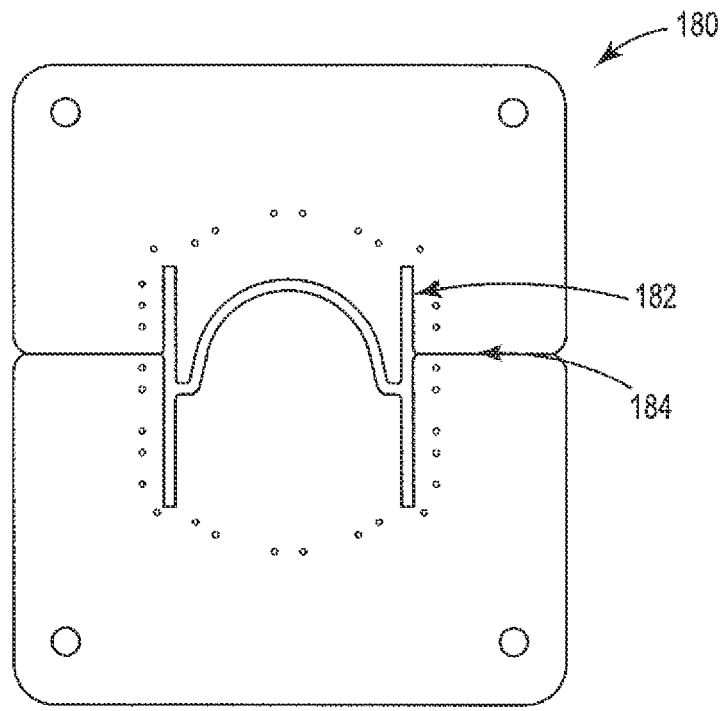
FIG. 14 is a top view of a wall protection plate.
Figure 15:
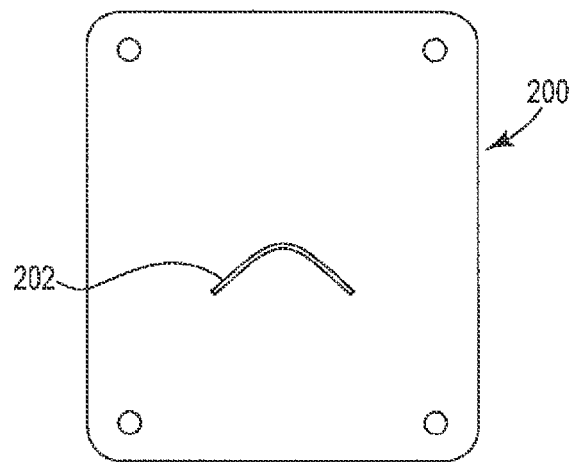
FIGS. 15 and 16 are top views of free margin cutting plates.
Figure 16:
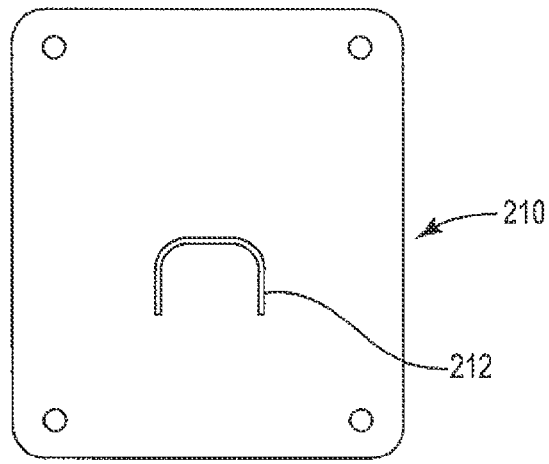

FIGS. 8 and 9 are top views of a bottom plate 80 of a final seam sewing fixture and a top plate 90 of a final seam sewing fixture, respectively, with an exemplary stitching pattern superimposed on each for purposes of illustration. These plates 80, 90 are used in the final step of sewing the pericardial material into a tube, or sewing the seam, as will be described in further detail below. Bottom plate 80 further includes at least one locating pin 82, and preferably includes at least two locating pins, as shown in FIG. 12. Plate 90 preferably also includes locating holes 92 in positions that correspond with the locating pins 82 for engagement with these locating pins. As with many of the other tooling fixtures described, the plate 80, 90 can include a number of additional holes located in various locations that can be used as tack holes for positioning the pericardial or tissue layers along with other tooling components, or for other purposes.

Figure 10:
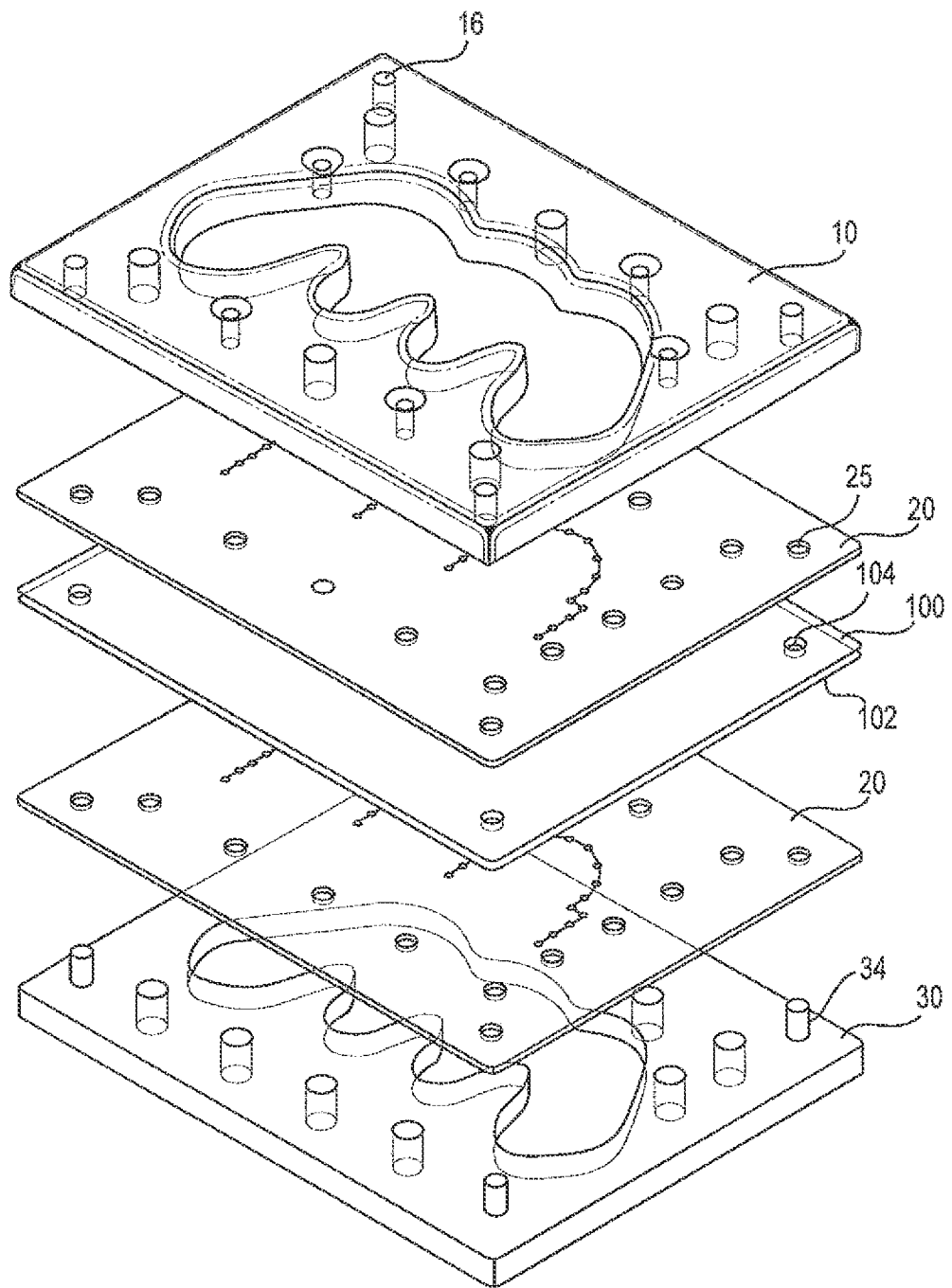
FIG. 10 is an exploded perspective view of multiple components and material layers involved in an initial sewing step for assembling a pericardial valve.

FIG. 10 is an exploded perspective view of multiple components and tissues involved in an initial sewing step for assembling a pericardial valve, utilizing some of the components described above relative to FIGS. 1-9. In particular, two layers of pericardial material or tissue 100, 102 are positioned as layers of an assembly including a number of plates and fixtures. In accordance with one embodiment of the invention, the layers of material 100, 102 can be a relatively flat sheet of pericardium material or tissue, which may be obtained, for example, from around a porcine heart It is understood that other donor species may alternatively be used, or that the material used may instead be a different type of tissue or material, such as a polymer or bio-engineered film.

Any pericardium material used may be at least partially fixed or cross-linked with a buffered gluteraldehyde solution or other solution at some point during the assembly process, in order to make the material easier for an operator to handle and manipulate. In one specific example, a piece of porcine pericardium is obtained, which is rinsed for approximately 10 minutes in a buffered gluteraldehyde solution to partially cross-link the material. U.S. Pat. No. 4,976,733 (Girardot), titled "Prevention of Prosthesis Calcification", describes a variety of additional exemplary methods of treating pericardium material that may be useful with the systems and methods of the present invention, along with methods for retarding or preventing the calcification of a prosthesis implanted in a mammal. However, such treatments to the material are optional and may be different depending on operator preference, the material chosen, and the like. The piece of pericardium can then be cut to a predetermined shape and size, such as the rectangular pieces of pericardium material 100, 102 illustrated in FIG. 10. If the material is thicker than desired, the thickness can be reduced using any of a number of available methods for effectively removing some of the thickness of the pericardium material without sacrificing an undesirable amount of the strength of the material. The sheets of material 100, 102 can also provided with locating holes 104 that preferably will align with the locating pins 34 of the bottom plate 30 of the sewing fixture frame.

The description of the positioning of the tooling components and tissue of an assembly are described herein as having "top" and "bottom" components, which generally corresponds to the figures. However, these terms are used for description purposes and are meant to describe the relative positioning of the components in an assembly. That is, the components could alternatively be reversed so that the top plate of the sewing fixture frame is actually on the bottom of the assembly, for example. Referring again to FIG. 10, a first sewing fixture template 20 is positioned on the top of the tissue layers 100, 102, while a second sewing fixture template 20 is positioned below the tissue layers 100, 102. A top plate 10 of the sewing fixture frame is positioned on top of the first sewing fixture template 20. A bottom plate 30 of the sewing fixture frame is positioned below the second sewing fixture template 20. All of the components, including the tissue layers, are preferably aligned so that the locating pins 34 of the bottom plate 30 of the sewing fixture frame can extend through their respective locating holes. The various additional holes in the components can be used as tack holes to help keep the tissue layers from sliding relative to each other. In that regard, a number of materials can be used for tacking, including pins, sutures, magnets, mechanical clamps, O-rings, or any other material or components that will exert adequate pressure or attachment features to keep the tissue layers 100, 102 from moving relative to each other. For ease in accurate assembly of the components, some or all of the tooling components can be at least partially transparent or opaque so that adjacent layers or components are visible or partially visible through some or all of the components.

After all of the components are assembled, an operator or an automated or semi-automated machine can stitch the layers of tissue 100, 102 to each other along the stitch pattern of the sewing fixture templates. The top plate 10 of the sewing fixture frame and the first (top) sewing fixture template 20 are then removed. A lower cutting fixture middle plate 70 is then inserted between the layers of tissue was shown in FIG. 11, and an upper cutting fixture middle plate 60 (which can also be referred to as a "spacer plate") is positioned on top of the upper layer of tissue 100. Alternatively, this upper cutting fixture middle plate 60, or spacer plate, can be inserted between the layers of tissue 100, 102, on the opposite side of the tissue layer from the lower cutting fixture middle plate 70. A top plate 50 of a cutting fixture is then placed on top of the assembly. This top plate 50 is used to define the free margin of the valve assembly. After the components are assembled in the way, the upper layer of tissue 100 is cut using a blade, die, stamp, or the like, by generally following the opening 52 in the top plate 50 of the cutting fixture. The placement of the lower cutting fixture middle plate 70 allows cutting of the upper layer of tissue 100 by cutting along or within the opening 53 in the top plate 50 of the cutting fixture, but protects the lower layer of tissue 102 from being cut. The components are all then disassembled, with only the stitched tissue being used in the next step of the process.

The stitched tissue assembly is then folded in half with the leaflet surface being on the inside of the fold. The locating holes 104 of the tissue layers 100, 102 should be aligned with each other after the tissue is folded to provide consistency of alignment in the final sewing step of FIG. 12. The folded tissue is then positioned as shown, with a sewing fixture template 40 adjacent to both its top and bottom sides, a bottom plate 80 of a final sewing fixture on the bottom of the assembly (with its locating pins 82 protruding upwardly), and a top plate 90 of a final sewing fixture on the top of the assembly. The locating pins 82 should extend through locating holes in the components to be sure the tissue is correctly aligned.

In this step, a reference tab of the stitched tissue should fall within the reference tab window of the final sewing fixture templates 40 (see reference tab window 44 of FIG. 4). The issue can then be sewn along the pattern line of the final sewing fixture templates 40 to create a seam for the valve that can be considered to be a one-seam valve. It is noted that the reference tab window 44 can be different than shown (e.g., taller, shorter, differently located, and the like), as long as it is consistent for all applications. The process described above relative to FIGS. 1-12 thus provides tooling and processes for making valves in a consistent, repeatable fashion due to the securing of the tissue layers relative to each other, the alignment of features throughout the process, and other factors.

As set out above, the two thicknesses of pericardium material can be attached to each other by sewing along a predefined pattern. The suture material used for the sewing process may be provided as a monofilament or multifilament structure made of natural or synthetic material (e.g., nylon or polypropylene), or may alternatively include an elongated metal or metal-composite thread or filament that is suitable for securing layers of pericardium material to each other. The stitching and suturing techniques will typically involve using an elongated thread-like material that may be attached to a needle to perform the securing function, which may either be done by have or with an automated machine. Referring again to FIG. 10, such techniques would typically include pushing the needle repeatedly through both thicknesses of the pericardium material in an outline shape that matches the desired pattern.

FIGS. 13-19 illustrate additional exemplary assembly sequences for making pericardial valves, including 2-dimensional leaflet construction and 3-dimensional leaflet construction. In these embodiments, individual leaflets are constructed, and several individual leaflets can be assembled into a multi-leaflet valve that has more than one side seam. Each of the constructed leaflets can be identical in size and shape to each other within a particular valve, or they can have different sizes, shapes, and/or patterns. First, with regard to a 2-dimensional leaflet construction, an assembly used for sewing includes a leaflet sewing plate on the bottom (e.g., sewing plate 160 illustrated in FIG. 13), then a wall layer of pericardial tissue, then a wall protection plate (e.g., wall protection plate 180 illustrated in FIG. 14), then a leaflet layer of pericardial tissue, then another leaflet sewing plate. In particular, the sewing plate 160 of FIG. 13 includes at least one locating hole 162, where this illustrated embodiment includes four of such locating hales in which locating pins can be placed for alignment of this plate with other components in the assembly and with the tissue layers. The sewing plate 160 further includes a number of tack holes or apertures 164, which are located generally around the perimeter of where the leaflet tissue will be positioned. There can be more or less tack holes 164 then illustrated, and they can be positioned differently than shown; however, there should be a sufficient number of tack holes 164 that can be used to help secure the tissue layers in place and prevent slippage between components during sewing.

The sewing plate 160 further includes a "margin of attachment" stitch pattern 166, which includes a series of holes 168 spaced from each other with suture channels 170 between adjacent holes 168. The holes 168 are provided as the location in which a needle will be inserted though the layers of tissue, and the channels 170 are provided for the portions of thread positioned between the holes 168. In this figure, a running stitch pattern is shown, although other stitch patterns can be used. One or more (preferably two) reference lines 172 are provided to show where the leaflet commissure will be created once the side seam is stitched in subsequent operations. Finally, at least one (preferably two) reference stitch lines 174 are provided, which include another series of holes and channels, as described above relative to other stitching patterns. The operator will use this line when stitching the "margin of attachment" stitches and will use the line with the side seam fixture to align the leaflets to each other.

The wall protection plate 180 is a plate that is positioned between two layers of pericardial tissue that are sewn together to create a leaflet. This plate 180 protects the wall tissue layer when the leaflet free margin is cut. This wall protection plate includes open slots 182 that allow the "margin of attachment" stitching and reference line stitching to go through to the wall protection plate. That is, because this plate will need to be removed from between the two layers of tissue, it cannot be sewn into the assembly. This plate is actually a two-piece assembly, as indicated by the break line 184, which allows the plate to be removed from the assembly once the layers of tissue are sewn together and the free margin is cut. The material that makes up these plate pieces is preferably: (1) thin enough to cause only a minimal gap between the two layers of tissue; (2) strong enough to withstand the cutting mechanism used to create the free margin of the leaflet; and (3) soil enough to not dull or otherwise adversely affect the free margin cutting mechanism.

Once the leaflets are sewn, such as is described above, the free margin can be cut. In order to do this, the top leaflet sewing plate is removed (i.e., the plate that is on top of the leaflet layer of pericardial tissue), and the free margin cutting plate (such as one of the cutting plates 200, 210 illustrated in FIGS. 15 and 16, respectively) is placed onto the leaflet layer of tissue. A cutting mechanism is then used to cut the designated free margin shape. Because the wall protection plate 180 is positioned between the leaflet and wall tissue, the cutting mechanism will only penetrate the leaflet layer of tissue. The channels 202, 212 illustrated in FIGS. 15 and 16, respectively, are examples of shapes that can be used for the free margin, which can be cut in any number of ways, such as by a blade, stamp, laser, or other cutting mechanism.

Figure 17:
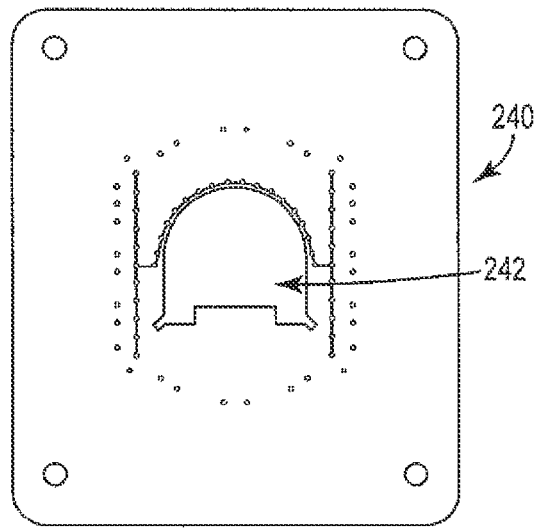
FIG. 17 is a top view of a sewing plate for 3-dimensional leaflets.
Figure 18:
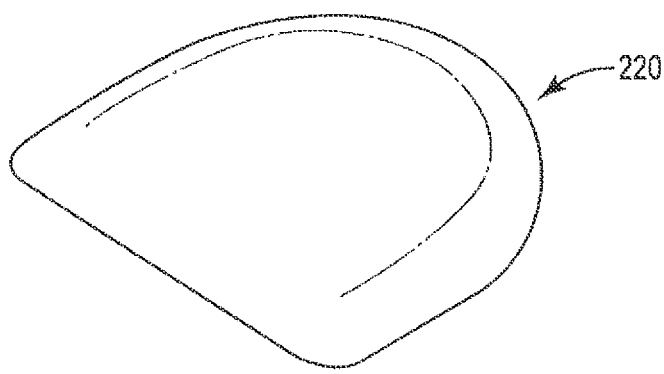
FIG. 18 is a perspective view of a 3-dimensional insert used for leaflet formation.

Next, with regard to a 3-dimensional leaflet construction, an assembly used for sewing includes a leaflet sewing plate on the bottom (e.g., sewing plate 160 illustrated in FIG. 13), then a wall layer of pericardial tissue, then a wall protection plate (e.g., wall protection plate 180 illustrated in FIG. 14), then a 3-dimensional mold (e.g., a mold or insert 220 of the type illustrated in FIG. 18), then a leaflet layer of pericardial tissue, then a 3-dimensional leaflet sewing plate (e.g., a leaflet sewing plate 240 of the type illustrated in FIG. 17). A similar sequence of steps and plate features to those described above can be followed; however, in this leaflet construction, a window is cut out of the 3-dimensional sewing plate 240 as designated by the aperture 242 to allow for a 3-dimensional insert (e.g., fee insert 220 of FIG. 18) to be placed under the leaflet layer of tissue, thereby increasing the leaflet surface area while maintaining a constant wall surface area. The stitch pattern of this sewing plate, including the "margin of attachment" and reference lines, remain on a 2-dimensional plane, which is important for maintaining both a constant surface area of the wall tissue and to provide for ease in manufacturability. The mold curvature provided by the insert 220 preferably matches that of the margin of attachment and also defines the amount of tissue used to create each leaflet. It is noted that in this contraction of a 3-dimensional leaflet, the free margin can be cut into the leaflet of tissue prior to sewing. In this way, the free margin cutting plate can be used to cut the tissue on a 2-dimensional plane.

Figure 19:
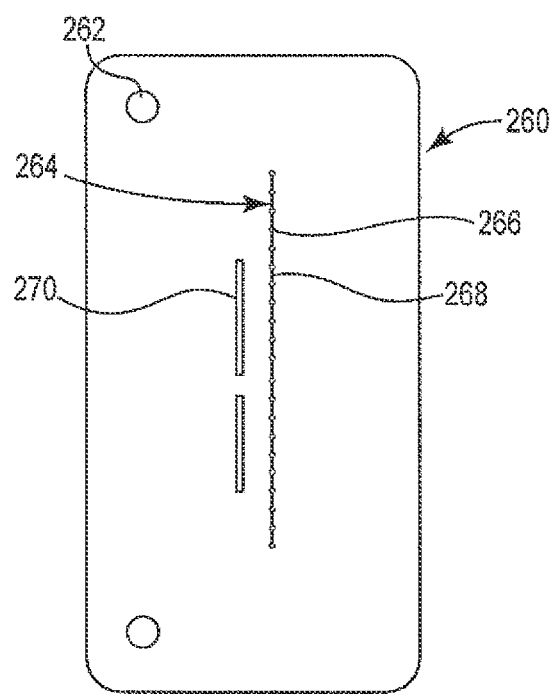
FIG. 19 is a top view of a side seam plate.

In order to form or make a leaflet assembly into a cylindrical or tubular valve using 2-dimensional or 3-dimensional leaflets, its side seams can be sewn using side seam plates 260 of the type illustrated in FIG. 19. In particular, an assembly is provided with a side seam plate 260 on which a first leaflet is placed with the leaflet side up, then a second leaflet is placed on the first leaflet with the leaflet side down, and then another side seam plate is placed on top of this second leaflet. Holes 262 of the side seam plates are provided to align with holes on the leaflet construction templates, in order to maintain alignment of the components. The side seam stitch pattern 264 consists of a series of holes 266 and channels 268 as described above relative to other stitching patterns. Finally, the reference line window 270 is provided for alignment with the reference lines that were stitched in the tissue with the sewing plates. This helps ensure that the two leaflets being stitched together are in proper alignment with the side seam stitch pattern and with one another. This general sequence is repeated to create three side seams for a tri-leaflet valve.

FIGS. 20-23 illustrate an exemplary valve assembly system 300 that can be used for making pericardial valves, including 2-dimensional leaflet constructions and 3-dimensional leaflet constructions, as desired. The system 300 can tightly secure pericardial tissue or other material during the processes of sewing and cutting the material, along with maintaining tissue tension, maintaining alignment of the tissue and assembly templates, and minimizing the transfer of tissue to multiple fixtures during the assembly thereof. In this way, a repeatable sewing and cutting technique can be established for the pattern shape, stitch length, and stitch placement. In addition, the system 300 uses features that make the fixturing easy to assemble and handle by the operator.

In order to provide the features described above, the valve assembly system 300 is provided with a robust and user-friendly pinning system. This system uses concentrated areas of multiple pins along the perimeter of the fixture for holding the tissue. In addition, one embodiment of the valve assembly system is a single-frame system, which provides for easy alignment of tissue. Overall, the assembly can be relatively thin so that it is a handheld device for an operator, although it is possible that the assembly is larger such that it is instead more appropriate for tabletop usage.

Valve assembly system 300 generally includes a top plate 302, a bottom plate 304, at least one frame clamp 306, and a slide pin cover 308. Although tissue is not shown in these Figures, tissue would be held between the top plate 302 and bottom plate 304 during the valve assembly process. Sewing and cutting templates can be slid in and out of the assembly 300 without transferring the tissue to any other fixtures. In this way, once the tissue is seemed between the top plate 302 and bottom plate 304, it will not need to be removed until the valve is completely sewn and assembled. Rather, pins 310 or other protrusions can extend from a top face of the bottom plate 304 to secure the tissue in place relative to the top plate 302 throughout the valve assembly process. In addition, peripheral locating pins can be used to ensure proper alignment of the tissue and templates relative to each other.

Figure 23:
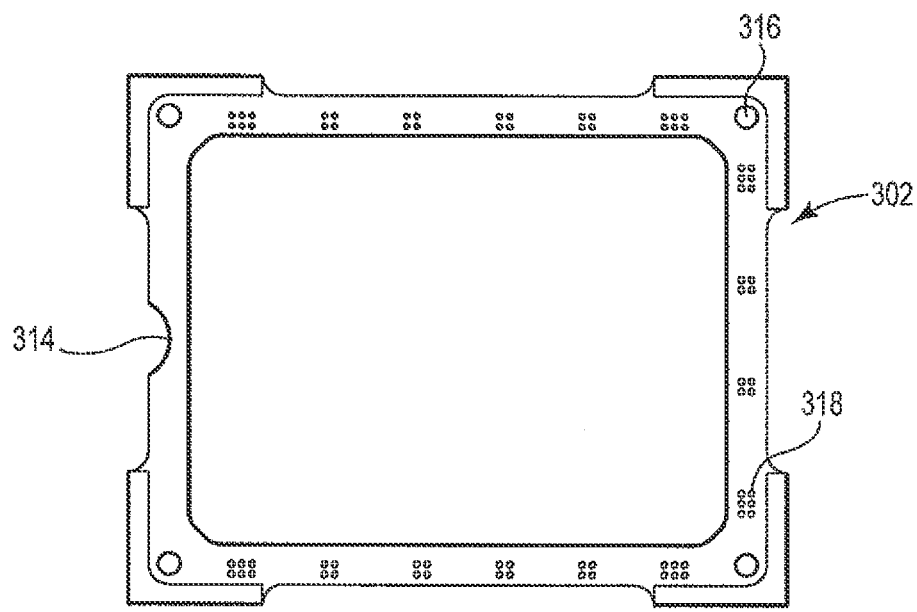
FIG. 23 is a bottom view of a top plate of the valve assembly system of FIGS. 20 and 21.

As illustrated in FIG. 23, top frame 302 may include multiple locating pin holes 316 for alignment with one or more sewing templates and the bottom plate 304. These pin holes 316 can extend through the entire thickness of the top plate 302 or only partially through its thickness. The top plate 302 may also be provided with a notch or contour 314 on one or more of its sides that can facilitate the movement of sewing and cutting templates relative to the assembly 300. The plate 302 can further include concentrated areas of holes 318 that can engage with the pins 310 that extend from the bottom plate 304. The top plate 302 may further optionally include a shelf step or recessed are (not shown) in its bottom surface that can accommodate the thickness of any sewing or cutting templates that are used.

Figure 21:
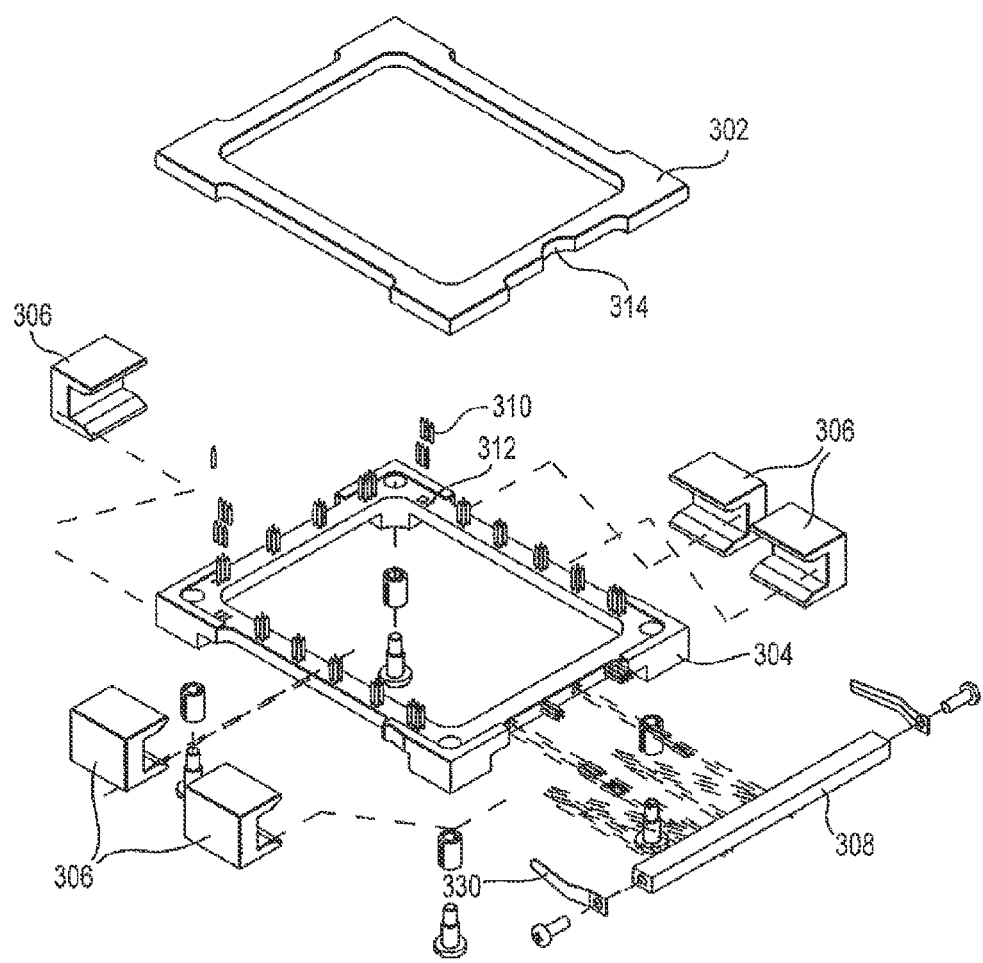
FIG. 21 is an exploded perspective view of the valve assembly system of FIG. 20.
Figure 22:
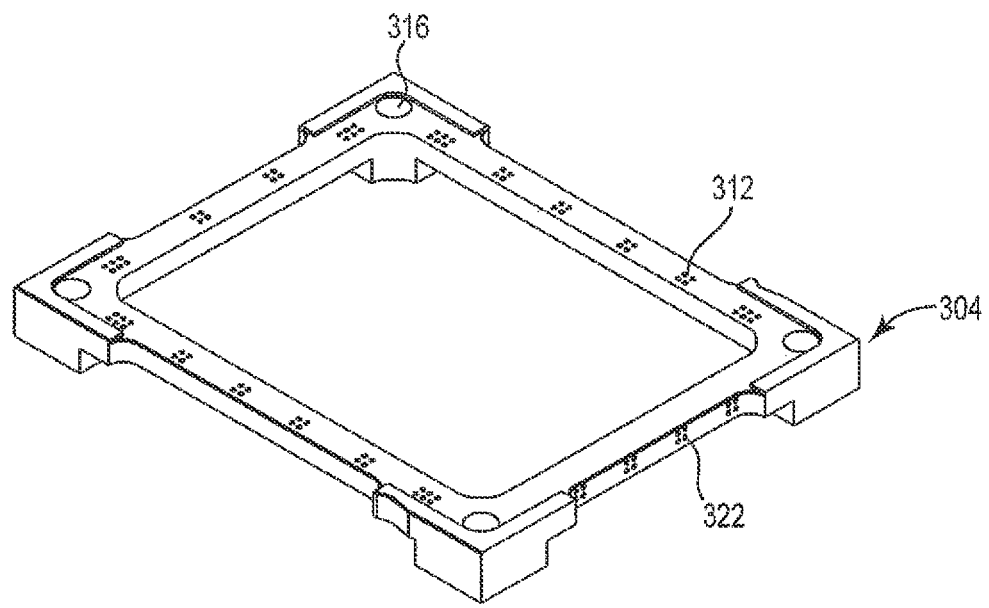
FIG. 22 is a perspective view of a bottom plate of the valve assembly systems of FIGS. 20 and 21.

Bottom plate 304, illustrated in FIG. 22, can also include locating pin holes 316 can be used for alignment with sewing and/or cutting templates and the top plate 302. The plate 304 can further include concentrated areas of holes 312 on its top surface into which pins 310 can be pressed, as is illustrated in FIG. 21. These pins 310 are preferably generally perpendicular to the face of the bottom plate 304 when they are inserted into the holes 312. As with the plate 302, the bottom plate 304 may optionally include a shelf stop or recessed area (not shown) in its top surface that can accommodate the thickness of sewing and/or cutting plates. Bottom plate 304 further includes concentrated areas of holes 322 on at least one of its sides. These holes 322 may also have pins 310 inserted therein, where these pins 310 can be used for engagement with a slide pin cover 308 or other component.

One embodiment of slide pin cover 308 may include concentrated areas of holes that correspond with the pins 310 that extend from the holes 322. The assembly may further include at least one finger spring 330 that extends from one or both sides of the pin cover 308. The spring or springs 330 can be used to secure the pin cover 308 to the system 300.

Figure 20:
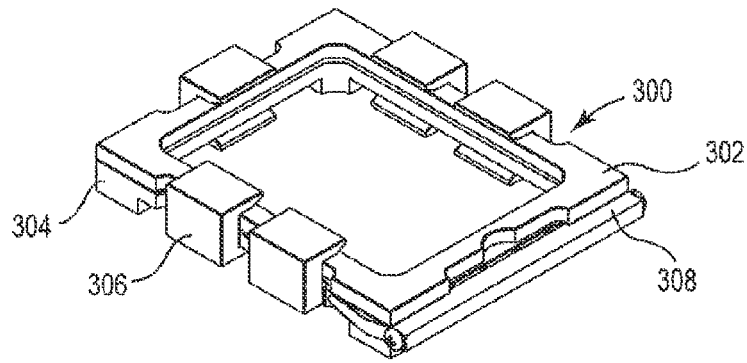
FIG. 20 is a perspective view of a valve assembly system in accordance with the invention.

System 300 further includes at least one frame clamp 306 for securing the top plate 302 to the bottom plate 304. The number of frame clamps 306 used can vary in order to achieve the desired clamping of the components to each other, but the assembly 300 preferably includes at least one clamp 306 on three of its sides. As illustrated in the embodiments of FIG. 20, the side of the system 300 that includes the slide pin cover 308 does not also have a clamp 306. In this way, any templates that are used can be slid into this side of the system. Each frame clamp 306 can include a tapered edge that allows it to slide onto the frame easily. In order to keep the components of the system stable relative to each other, the clamps 306 are preferably designed or chosen to provide a snug fit between components. However, the clamp 306 can also be relatively low profile so that the overall size of the system 300 is not increased by the clamp size.

In many of the embodiments described herein, the pericardial valve is prepared to include three leaflets, but may optionally have more or less than three leaflets, which can be formed by varying the number of leaflet and outer tube components. The three leaflet embodiment can be used is areas of the heart that typically have a three leaflet valve, such as the pulmonary valve and aortic valve, although the three leaflet embodiment can also be used as a replacement for the two leaflet mitral valve. Alternatively, a two leaflet or single leaflet embodiment of the valve of the invention is contemplated, which can be used in areas of the heart that typically have a three leaflet valve, such as the pulmonary valve, for example. Certain considerations for blood flow will determine particular parameters of the valve used.

Once a tissue valve is manufactured using the above techniques and tooling, the tissue valve can be attached within a stent, where the stent can be secured to the valve segment in a variety of ways. One procedure that can be used is to suture certain areas of the stent to the valve segment. The suture material may be provided as a monofilament or multifilament structure made of natural or synthetic materials (e.g., nylon or polypropylene), or may alternatively include an elongated metal or metal-composite thread or filament that is suitable for permanently securing the stent to the valve segment in accordance with the present invention. The number and location of suture points can vary, but should include an adequate number of connection points that are positioned in predetermined locations that prevent movement of the stent relative to the valve segment, particularly during the compression of the stent for percutaneous delivery and expansion of the stent for its deployment.

The stented valve can be subjected to suitable chemical fixation and/or bioburden reduction treatments, which may vary considerably depending on the particular requirements for storage and use of the stented valve. Chemical fixation helps to preserve the tissue, render it inert, reduce the risk of host rejection, and/or the like. Chemical fixation may occur by submerging the valve in a suitable reagent for a period of about 3 hours under slight pressure and ambient temperature and then for 72 hours under ambient pressure and temperature. By way of example, a 0.2% by weight gluteraldehyde solution at physiological pH and being phosphate buffered may be used for chemical fixation. The valve may then be stored in a suitable storage reagent (e.g., an aqueous solution containing 0.2% by weight gluteraldehyde) until subsequent use. Bioburden reduction may be carried out by submerging the tissue in a suitable reagent for a period of 48 to 72 hours at ambient temperature. By way of example, an aqueous solution containing 1% by weight gluteraldehyde and 20% by weight isopropyl alcohol at physiological pH and being phosphate-buffered may be used for bioburden reduction. This solution would be suitable for use as a packaging solution as well. A variety of fixation tines, concentrations, pH levels and chemicals can be used in accordance with the invention. After suitable treatments to the valve are complete and after appropriate rinsing of the valve, the device can be used for implantation into a human.

The stented valve may then be used with a system for delivering the valve segment to the desired location within a patient. The delivery system may include, for example, an outer sheath overlying an inner balloon catheter, where the outer sheath includes an expanded distal portion, within which the stented valve is located. The stented valve can be compressed around a single or double balloon located on the inner catheter. A tapered tip is mounted to the distal end of the inner catheter and serves to ease the passage of the delivery system through the patient's vasculature. The system also may include some type of guidewire to guide the delivery system to its desired implant location. Another alternative delivery system that can be used, in particular, for stented valves having a self-expanding stent, includes a catheter that does not have balloons, but instead includes a sheath or other mechanism that maintains the self-expanding stent in its compressed condition until it is desired to allow it to expand. When such a self-expanding stent is properly positioned in the patient, the mechanism that keeps the stent compressed can be retracted or otherwise removed to allow for expansion of the stent against the vessel walls.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing form the scope of the invention. Thus, the scope of the present invention should not be limited to the structures described herein, but by the structures described by the language of the claims and the equivalents of those structures.

What is claimed is:

1. A method of assembling a prosthetic heart valve, comprising the steps of:
   providing first and second sheets of material, each comprising first and second 5 opposite surfaces and positioning the first and second sheets of material relative to each other so that at least a portion of the first side of the second sheet of material is in contact with at least a portion of the second side of the first sheet of material;
   positioning a first sewing fixture template adjacent to the first side of the first sheet of material and positioning a second sewing fixture template adjacent to the second side of the second sheet of material, wherein the first and second sewing fixture templates each comprise a sewing pattern;
   positioning a top sewing fixture frame plate adjacent to the first sewing fixture template, wherein the top plate comprises a central opening through which the sewing pattern of the first sewing fixture template can be accessed;
   positioning a bottom sewing fixture frame plate adjacent to the second sewing fixture template, wherein the bottom plate comprises a central opening through which the sewing pattern of the second sewing fixture template can be accessed;
   stitching the first and second sheets of material to each other along the sewing patterns of the first and second sewing fixture templates;
   removing the top sewing fixture frame plate and the first sewing fixture template;
   inserting a lower cutting fixture middle plate between the first and second sheets of material and positioning a top cutting fixture plate adjacent to the first side of the first sheet of material, wherein the top cutting fixture plate comprises a central opening;
   cutting the first sheet of material through the central opening of the top cutting fixture plate;
   removing the first and second sheets of material and folding the material sheets along a fold line so that a top surface and a bottom surface of the assembled material are facing in opposite directions;
   positioning a first final sewing fixture template adjacent to the top surface of the assembled material and positioning a second final sewing fixture template adjacent to the bottom surface of the assembled material, wherein the first and second final sewing fixture templates each comprise a pattern line;
   positioning a first final seam sewing fixture adjacent to the first final sewing fixture template and positioning a second final sewing seam fixture adjacent to the second final sewing fixture template; and
   stitching the assembled material along the pattern line of the first and second final sewing fixture templates.

2. The method of claim 1, further comprising the step of inserting an upper cutting fixture middle plate between the first side of the first sheet of material and the top cutting fixture plate prior to the step of cutting the first sheet of material.

3. The method of claim 1, further comprising the step of inserting an upper cutting fixture middle plate between the first and second sheets of material prior to the step of cutting the first sheet of material.

4. The method of claim 1, wherein the first and second sheets of material comprise pericardial tissue.

5. The method of claim 1, wherein the first and second sheets of material comprise substantially flat sheets of material.

6. The method of claim 1, wherein the bottom sewing fixture frame plate comprises at least one locating pin and wherein the first and second sheets of material each comprise at least one aperture through which one locating pin can be inserted.

7. The method of claim 6, wherein the at least one locating pin is alignable with at least one of the components positioned above it during the steps of assembling the prosthetic valve.

8. The method of claim 1, further comprising the step of attaching the assembled material to a stent after the step of stitching the assembled material along the pattern line of the first and second final sewing fixture templates.

9. The method of claim 1, wherein the sewing pattern of the first and second sewing fixture templates comprises a plurality of holes spaced from each other and a channel positioned between each adjacent pair of holes.

10. The method of claim 9, wherein a diameter of each of the holes is larger than the width of each of the channels.

11. The method of claim 1, wherein the sewing pattern of the first sewing fixture template is aligned with the sewing pattern of the second sewing fixture template.

12. A valve assembly system for use in making prosthetic valves, the system comprising:
   a top plate having a first surface comprising multiple locating pin holes and a locating pin extending from each of the holes;
   a bottom plate adjacent to the top plate, wherein the bottom plate comprises a first surface comprising multiple locating pin holes, each of which is aligned and engaged with a locating pin extending from the top plate;
   at least one removable frame clamp contacting an outwardly facing surface of the top plate and an outwardly facing surface of the bottom plate; and
   a removable slide pin cover removeably attached to a first edge of the bottom plate.

13. The valve assembly system of claim 12, further comprising multiple locating pin holes along the first edge of the bottom plate and a locating pin extending from each of the holes for engagement with the removable slide pine cover.

* * * * *

UNITED STATES PATENT AND TRADEMARK OFFICE
CERTIFICATE OF CORRECTION

| | | |
|---|---|---|
| PATENT NO. | : 8,511,244 B2 | Page 1 of 1 |
| APPLICATION NO. | : 13/656247 | |
| DATED | : August 20, 2013 | |
| INVENTOR(S) | : Holecek et al. | |

It is certified that error appears in the above-identified patent and that said Letters Patent is hereby corrected as shown below:

In the Claims

Column 14, Line 62, Claim 13, "removable slide pine cover" should read -- removable slide pin cover --

Signed and Sealed this
Twenty-third Day of December, 2014

Michelle K. Lee
*Deputy Director of the United States Patent and Trademark Office*